United States Patent
Zhao et al.

(10) Patent No.: US 9,851,259 B2
(45) Date of Patent: *Dec. 26, 2017

(54) INFRARED DETECTOR

(71) Applicant: MivaLife Mobile Technology, Inc., George Town (KY)

(72) Inventors: Hongjuan Zhao, Zhuhai (CN); Yueqiong Wang, Zhuhai (CN); Kai Li, Guangzhou (CN); Hangqiang Chen, Zhuhai (CN); Shangyu Guo, Foshan (CN); Shaodong Ma, Zhuhai (CN); Qin Yuan, Zhuhai (CN)

(73) Assignee: MivaLife Mobile Technology, Inc., George Town (KY)

( * ) Notice: Subject to any disclaimer, the term of this patent is extended or adjusted under 35 U.S.C. 154(b) by 0 days.

This patent is subject to a terminal disclaimer.

(21) Appl. No.: 15/237,549

(22) Filed: Aug. 15, 2016

(65) Prior Publication Data

US 2017/0160140 A1 Jun. 8, 2017

Related U.S. Application Data

(63) Continuation-in-part of application No. 14/491,225, filed on Sep. 19, 2014, now Pat. No. 9,418,532.

(30) Foreign Application Priority Data

Mar. 26, 2014 (CN) .......................... 2014 1 0116794

(51) Int. Cl.
*G08B 17/00* (2006.01)
*G01J 5/18* (2006.01)
(Continued)

(52) U.S. Cl.
CPC .................. *G01J 5/18* (2013.01); *A61B 5/01* (2013.01); *G01J 5/0025* (2013.01); *G01J 5/0066* (2013.01); *G01J 5/026* (2013.01); *G01J 5/028* (2013.01); *G01J 5/089* (2013.01); *G01J 5/0846* (2013.01); *G01J 5/0893* (2013.01);
(Continued)

(58) Field of Classification Search
CPC ....... G01J 5/18; G01J 5/34; G01J 5/12; G08B 21/0469
USPC ............ 340/584, 541, 565, 566, 567, 545.3; 250/339.15, 352, 338.1, 338.3, 339.04, 250/339.11, 341.8
See application file for complete search history.

(56) References Cited

U.S. PATENT DOCUMENTS 4,912,748 A 3/1990 Horii et al.
6,597,287 B1 7/2003 Steinel
(Continued)

*Primary Examiner* — Toan N Pham
(74) *Attorney, Agent, or Firm* — Fish & Richardson P.C.

(57) ABSTRACT

Methods, systems, and apparatus, for an infrared detector are provided. In one aspect, an infrared detector is provided that includes a pyroelectric sensor; a controller for receiving a trigger signal outputted by the pyroelectric sensor; a thermopile sensor, wherein the controller starts the thermopile sensor after receiving the trigger signal output by the pyroelectric sensor; and an alarm, wherein the controller controls the alarm to generate an alarm signal in response to a determination that a difference between a current temperature and a background temperature detected by the thermopile sensor is larger than a threshold value and a determination that the areas of the thermopile sensor activated correspond to a human being.

21 Claims, 2 Drawing Sheets

(51) Int. Cl.
*G01J 5/00* (2006.01)
*G01J 5/02* (2006.01)
*G01J 5/08* (2006.01)
*A61B 5/01* (2006.01)
*G01K 1/20* (2006.01)
*G08B 21/04* (2006.01)
*G08B 21/22* (2006.01)
*G01J 5/12* (2006.01)
*G01J 5/34* (2006.01)
G01J 5/10 (2006.01)
G01J 5/06 (2006.01)

(52) U.S. Cl.
CPC . *G01J 5/12* (2013.01); *G01J 5/34* (2013.01); *G01K 1/20* (2013.01); *G08B 21/0469* (2013.01); *G08B 21/22* (2013.01); *G01J 2005/0048* (2013.01); *G01J 2005/0085* (2013.01); *G01J 2005/068* (2013.01); *G01J 2005/106* (2013.01)

(56) References Cited

U.S. PATENT DOCUMENTS

| | | | |
|---|---|---|---|
| 6,677,589 B2 * | 1/2004 | Hironaka | G01J 5/34 250/336.1 |
| 6,819,240 B2 * | 11/2004 | Iwasawa | G08B 13/183 340/541 |
| 7,541,924 B2 | 6/2009 | Elwell | |
| 9,418,532 B2 | 8/2016 | Zhao et al. | |
| 2012/0229283 A1 | 9/2012 | McKenna | |

* cited by examiner

INFRARED DETECTOR

CROSS-REFERENCE TO RELATED APPLICATIONS

This application is a continuation-in-part of and claims the benefit of U.S. patent application Ser. No. 14/491,225, which claims the benefit under 35 U.S.C. §119 of the filing date of Chinese Patent Application No. 201410116794.8, for Smart Infrared Detector and Working Method Thereof, which was filed on Mar. 26, 2014. The foregoing applications are incorporated here by reference.

BACKGROUND

The present specification relates to infrared detectors.

Infrared detectors are often used to measure temperature changes within an area such as a room being monitored. One typical type of infrared detector includes a pyroelectric sensor. When a surface temperature of the pyroelectric sensor's dielectric changes, the dielectric generates an electric charge. In particular, polarization of the material forming the dielectric surface changes in response to a change in temperature, which generates a voltage across the dielectric. When the surface temperature rises, the polarization strength in the dielectric reduces, which results in a release of charge by the dielectric. The generated charge gradually drifts away from the dielectric surface. Infrared radiation incident upon the dielectric of the pyroelectric sensor continues. When the surface temperature of the dielectric reaches equilibrium, i.e., a constant temperature, it stops releasing a charge, and no signal is output. Thus, the pyroelectric sensor is used to detect temperature changes in an area being monitored.

Once a person enters the area being monitored, a change in the temperature of the area occurs. The infrared detector can detect these temperature changes, e.g., based on the pyroelectric sensor. Thus, based on signals outputted by the infrared detector, it can be determined whether or not someone enters the area being monitored.

However, conventional infrared detectors can only identify temperature changes and cannot detect when there is a static infrared signal source in the area being monitored. For example, if an elderly person enters the area being monitored and falls down in the area, a conventional infrared detector can only determine if the temperature changes in the area being monitored. Thus, the detector can determine that someone enters or leaves the area being monitored, but cannot determine that a continuous and static infrared signal source exists in the area being monitored. Consequently, the conventional detector would fail to determine that someone fell down in the area being monitored and as a result the detector cannot generate an alarm in response.

In some typical scenarios that require nursing care and monitoring, web cameras are often used to monitor the area. The camera is used to capture video images of the area and transmits the video images, for example, to a nursing station.

However, cameras generally have high power consumption and are powered by city electricity, which restricts installation and applications of the web cameras. In addition, since the web cameras produce images of the area being monitored, protecting the privacy of persons in the area being monitored restricts their use as well. For example, the web cameras typically cannot be installed in washing rooms and bedrooms.

SUMMARY

An infrared detector is described in this specification that can detect a static infrared signal source while having low power consumption.

In general, one innovative aspect of the subject matter described in this specification can be embodied in infrared detectors that include a pyroelectric sensor; a controller for receiving a trigger signal outputted by the pyroelectric sensor; a thermopile sensor, wherein the controller starts the thermopile sensor after receiving the trigger signal output by the pyroelectric sensor; a timer, wherein the controller starts the timer after receiving the trigger signal output by the pyroelectric sensor, and starts the thermopile sensor after a counted time is ended; and an alarm, wherein the controller controls the alarm to generate an alarm signal in response to a determination that a difference between a current temperature and a background temperature detected by the thermopile sensor is larger than a threshold value and a determination that the areas of the thermopile sensor activated correspond to a human being.

The foregoing and other embodiments can each optionally include one or more of the following features, alone or in combination. In particular, one embodiment includes all the following features in combination. The infrared detector further includes a processing engine configured to analyze data from the thermopile sensor to determine whether a human being is detected. The infrared detector further includes a processing engine configured to use a wireless circuit to communicate data from the thermopile sensor to a remote analysis location and to receive a result of the analysis. The alarm is a wireless alarm circuit. The wireless alarm circuit is a wireless radio frequency (RF) circuit, a Wi-Fi signal transmitting circuit, or a Bluetooth signal transmitting circuit. The infrared detector further includes a battery module, for supplying power to the pyroelectric sensor and the thermopile sensor. The pyroelectric sensor detects entry of an individual to a region being monitored by the infrared sensor and wherein the thermopile sensor determines whether the individual remains in the region being monitored.

In general, one innovative aspect of the subject matter described in this specification can be embodied in methods that include the actions of using a thermopile sensor of an infrared detector to determine a background temperature of an area being monitored; using a pyroelectric sensor of the infrared detector to determine whether a temperature in the area being monitored has changed; and in response to a determination that the temperature has changed: using a thermopile sensor to determine a current temperature in the area being monitored including initiating a timer to count down a specified amount of time; comparing the determined current temperature to the background temperature; and based on the comparing, determining whether a difference between the determined current temperature and the background temperature satisfies a threshold value; in response to determining that the difference satisfies the threshold value, determining whether the thermopile sensor data corresponds to a human being; and in response to determining that the thermopile sensor data corresponds to a human being, generating an alarm.

The foregoing and other embodiments can each optionally include one or more of the following features, alone or in combination. In particular, one embodiment includes all the following features in combination. Determining whether the thermopile sensor data corresponds to a human being comprises: determining the areas of an absorption region of the thermopile sensor triggered by infrared signals; determining an outline or shape of the areas; and determining whether the outline or shape of the areas corresponds to a human being. Determining whether the thermopile sensor data corresponds to a human being comprises: compressing the thermopile sensor data; transmitting the compressed thermopile sensor data to a remote location; and receiving a determination of whether the thermopile sensor data corresponds to a human being from the remote location. In response to determining that the thermopile sensor data does not correspond to a human being, discontinuing the alarm process. In response to the timer time elapsing, using the thermopile sensor to determine the current temperature of the area being monitored. Generating the alarm includes using a wireless alarm circuit. The wireless alarm circuit is a wireless radio frequency (RF) circuit, a Wi-Fi signal transmitting circuit, or a Bluetooth signal transmitting circuit.

In general, one innovative aspect of the subject matter described in this specification can be embodied in infrared detectors that include a pyroelectric sensor; a controller for receiving a trigger signal outputted by the pyroelectric sensor; a thermopile sensor, wherein the controller starts the thermopile sensor after receiving the trigger signal output by the pyroelectric sensor; and an alarm, wherein the alarm is triggered by the controller in response to determining that detected signals from the thermopile sensor correspond to a human being; wherein the pyroelectric sensor detects entry of an individual to a region being monitored by the infrared sensor and wherein the thermopile sensor determines whether the individual remains in the region being monitored.

In general, one innovative aspect of the subject matter described in this specification can be embodied in methods that include the actions of using a thermopile sensor of an infrared detector to determine a background temperature of an area being monitored; using a pyroelectric sensor of the infrared detector to determine whether a temperature in the area being monitored has changed wherein the pyroelectric sensor detects entry of an individual to a region being monitored by the infrared detector; and in response to a determination by the pyroelectric sensor that the temperature has changed using the thermopile sensor to determine whether the individual remains in the region being monitored: using a thermopile sensor to determine a current temperature in the area being monitored; determining an outline or shape of an area of an absorption region of the thermopile sensor in which the current temperature is different from the background temperature; determining whether the outline or shape corresponds to a human being; and in response to determining that the outline or shape corresponds to a human being, generating an alarm.

The subject matter described in this specification can be implemented in particular embodiments so as to realize one or more of the following advantages. An infrared sensor is provided that can detect both changes in temperature within an area being monitored as well as detect static infrared sources. As a result, the infrared detector can improve monitoring of an area to detect static sources particularly in cases of monitoring individuals particularly those under nursing care while minimizing the impact on individual privacy. Additionally, the infrared detector can evaluate thermopile measurements to determine whether or not the detection corresponds to a human being or not. This can reduce instances of false alarms triggered, for example, by pets or other non-human temperature sources.

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

This specification describes an infrared detector. The infrared detector is configured to include both a pyroelectric sensor and a thermopile sensor. The infrared detector can be used to monitor particular regions. For example, the infrared detector can be used to detect activities of persons in a specific area being monitored such as a particular room, thereby being applicable to circumstances that involve monitoring of vulnerable individuals, e.g., nursing.

Figure 1:
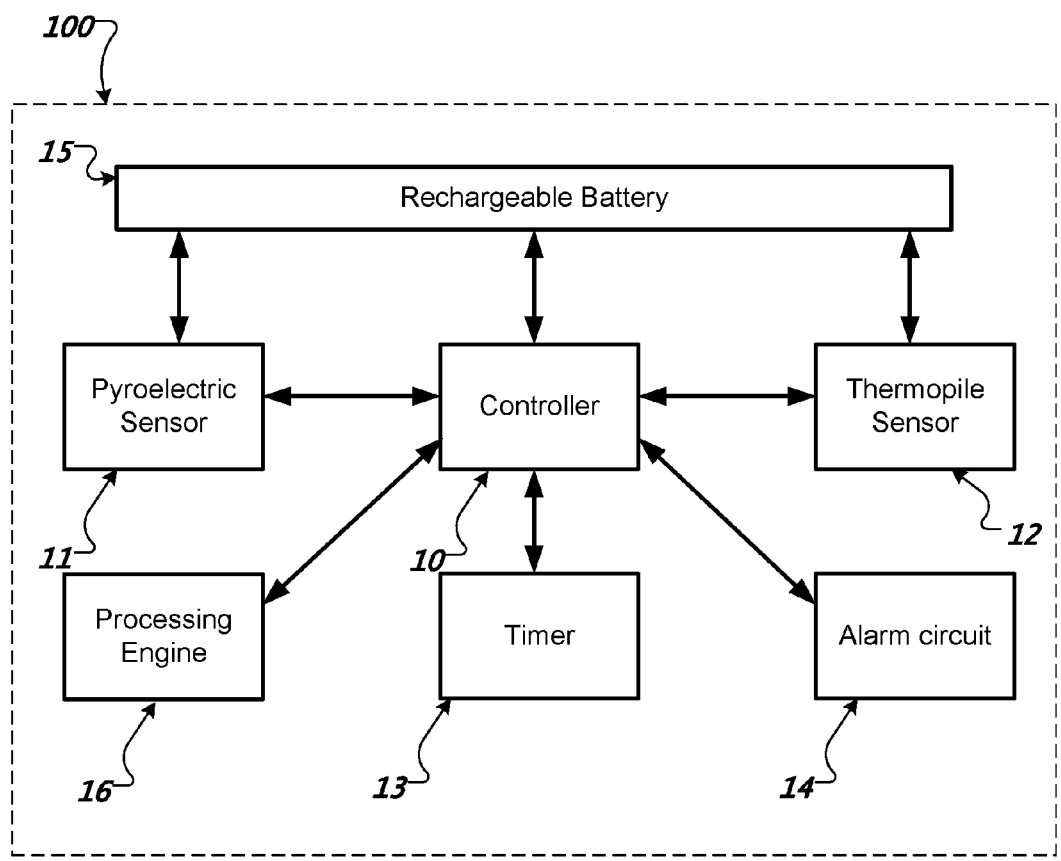
FIG. 1 is a block diagram of an example structure of an infrared detector.

FIG. 1 is a block diagram of an example structure of an infrared detector 100. The infrared detector 100 includes a controller 10, a pyroelectric sensor 11, a thermopile sensor 12, a timer 13, a wireless radio frequency (RF) circuit 14, a rechargeable battery 15, and a processing engine 16.

The controller 10 controls operations of the pyroelectric sensor 11 and the thermopile sensor 12, and receives signals sent by the pyroelectric sensor 11 and the thermopile sensor 12. Moreover, the controller 10 controls the wireless RF circuit 14 to generate an alarm signal when triggered.

The pyroelectric sensor 11 is used to determine whether anyone enters an area being monitored such that the temperature changes. When someone enters the area being monitored and causes temperature changes, e.g., when a movable infrared signal source enters the area being monitored, a surface temperature of the pyroelectric sensor's 11 dielectric changes and the dielectric releases some electric charge. The pyroelectric sensor 11 is triggered and sends a trigger signal to the controller 10.

The thermopile sensor 12 includes a plurality of thermocouple sensors coupled in series or in parallel. The thermopile sensor 12 is used to monitor a static temperature in the area being monitored. In particular, the thermopile sensor 12 detects a static infrared signal source, converts the detected temperature into an electrical signal, and determines the temperature in the area being monitored based on the electrical signal. In some implementations, the thermopile sensor 12 enters a sleeping mode in which it does not maintain a working status continuously to save the electrical energy consumed by the infrared detector 100.

The timer 13 starts counting down a specified amount of time under the control of the controller 10. Once the counted time was elapsed, the timer 13 outputs a break request signal (BRS) to the controller 10. The break request signal informs the controller 10 that the counted time is ended. The specific amount of time set by the timer 13 may be a time set within the controller 10. Additionally, in some implementations, the timer is built as part of the controller 10.

The wireless RF circuit 14 provides the alarm for the infrared detector 100. The wireless RF circuit 14 sends an alarm signal, in response to a command from the controller 10, in a form of a wireless RF signal to a backend control center, e.g., a backend computer or server. After receiving the alarm signal, the control center informs the authorized individuals of the alarm. For example, in a nursing context, the controlling center can inform a nursing staff to provide help to the person associated with the alarm. The control center can be part of a cloud based distributed system.

Alternatively, in some other implementations, the alarm is a wireless alarm circuit in another form, e.g., a Wi-Fi signal transmitting circuit, or a BLUETOOTH signal transmitting circuit. These alarm circuits send wireless signals to the backend control center. In addition, the alarm may be a sound and light alarm circuit integrated with the infrared detector, e.g., a light emitting diode (LED) or buzzer to provide a local audible alarm. The individuals around the infrared detector 100 respond to the alarm generated by the sound and light alarm circuit of the infrared detector 100.

The rechargeable battery 15 provides a battery module for the infrared detector 100 and is used to supply power to the controller 10, the pyroelectric sensor 11, and the thermopile sensor 12. Since the pyroelectric sensor 11 and the thermopile sensor 12 consume low levels of electrical energy, a typical rechargeable battery 15 can supply a stable low-voltage direct current (DC) to satisfy the operational requirements of the pyroelectric sensor 11 and the thermopile sensor 12.

The processing engine 16 can be used to evaluate signals detected by the thermopile sensor 12. In particular, the processing engine 16 can analyze the signals directly or provide the signals to a remote location, e.g., through one or more networks, for analysis. The analysis can be a determination of whether the signals detected by the thermopile sensor 12 correspond to a human being or not. Additional details on the analysis applied to the thermopile sensor data is described below with respect to FIG. 2.

In some implementations, the processing engine 16 can include a processor and firmware configured to analyze the locations of the thermopile sensor 12 that detect infrared signals in order to make a determination about the shape of the detected object corresponding to a human being or not.

In some implementations, the processing engine 16 is coupled to the wireless RF circuit 14 or other wireless circuit for communicating the thermopile sensor data as well as receive results of the analysis, for example, from the control center. The control center can perform the analysis in a similar manner as the described for the local analysis by the processing engine 16 except the control center can use a computer including particular software applications to perform the analysis rather than firmware.

The processing engine 16 can also include a compressor configured to compress the thermopile sensor data before transmission by the wireless RF circuit 14. The compressor can use one or more particular compression algorithms suitable for the sensor data to reduce the size of the data transmitted to the control center.

Figure 2:
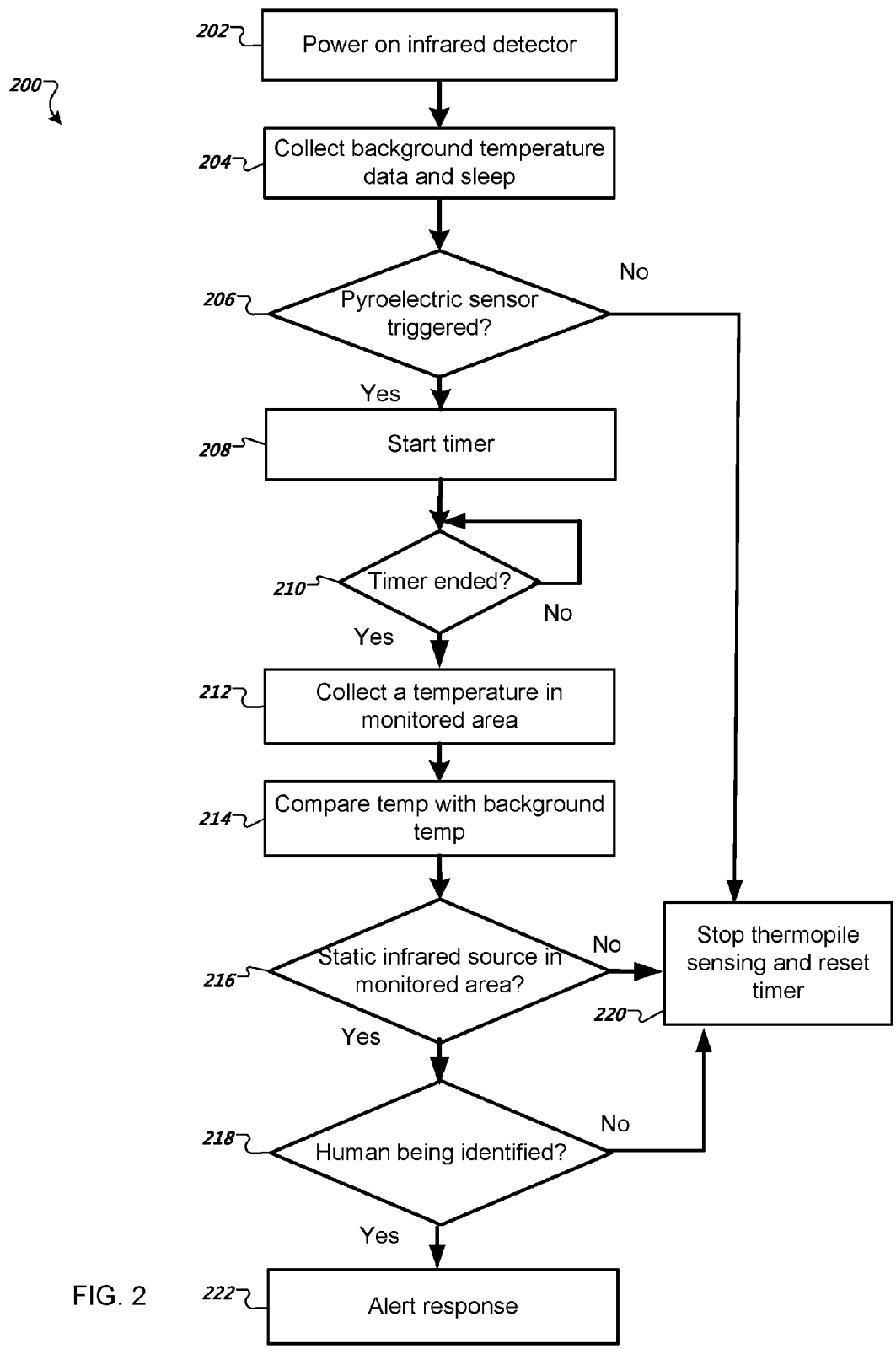
FIG. 2 is a flow chart of an example process for using an infrared detector.

FIG. 2 is flow chart of an example process 200 for using an infrared detector, e.g., infrared detector 100 of FIG. 1. The infrared detector is activated 202. For example, a battery, e.g., rechargeable battery 15, supplies power to a controller, a pyroelectric sensor, and a thermopile sensor of the infrared detector. The controller can be the controller 10, the pyroelectric sensor can be the pyroelectric sensor 11, and the thermopile sensor can be the thermopile sensor 12 of FIG. 1. The thermopile sensor of the infrared detector collects a background temperature in an area being monitored, and outputs the collected temperature data to the controller. The controller stores the background temperature data. Then, the thermopile sensor enters a sleeping status (204).

The pyroelectric sensor determines whether anyone enters the area being monitored causing a temperature change in the area. If it is determined that someone enters the area being monitored, the pyroelectric sensor is triggered, and outputs a trigger signal to the controller (206). If it is determined that someone has not entered the area being monitored, the thermopile sensor terminates the working status (220).

The controller initiates a timer, e.g., the timer 13 of FIG. 1, to start counting down the specified time (208). The controller determines whether the counted time is ended (210). If it is determined that the counted time has ended, yes branch of 210, the controller starts the thermopile sensor. The thermopile sensor collects a temperature in the area under detection, converts the temperature into an electrical signal, and outputs it to the controller (212). If the counter time has not ended, no branch of 210, the timer continues to count down and the determination is repeated. In some implementations, a subsequent detection of someone entering the area by the pyroelectric sensor resets the timer.

The controller compares the collected current temperature in the area being monitored with the background temperature (214). The controller determines whether any static infrared signal source exists in the area being monitored based on a comparison result (216).

If the controller determines that the temperature in the area under detection has not changed or that the difference between the current temperature in the area under detection and the background temperature is smaller than a threshold value, no branch of 216, the controller determines that no static infrared signal source exists in the area under detection, the thermopile sensor terminates the working status, and the timer is reset to zero (220).

If the controller determines that the current temperature of the area being monitored is inconsistent with the background temperature, or a difference there-between is larger than a threshold value, yes branch of 216, it is determined that a static infrared signal source exists in the area under detection.

In response to the determination that there is a static infrared signal source, the controller determines whether the static infrared signal source corresponds to a human being (218). The determination can be performed locally in concert with a processing engine, e.g., processing engine 16, or through a combination of local and remote resources.

The determination is based on an analysis of the thermopile sensor data. In particular, the thermopile sensor has an infrared absorbing region, for example, an array of thermocouples. Infrared signals coming from different locations within a field of view of the sensor are incident on different portions of the absorbing region. The pattern of locations on the absorbing region that detect infrared signals can be analyzed to make a determination as to the nature of the detected object. For example, the shape or outline of the area of the absorbing region detecting an infrared signal can be determined to correspond to a human shape. In some implementations, pattern matching techniques are used to compare the identified outline/shape from the sensor to one or more template patterns.

The analysis can be performed directly by the processing engine with an output result provided to the controller. In some implementations, the thermopile sensor data is transmitted to a remote analysis location where the analysis is performed. The results of the analysis can be returned to the processing engine or directly to the controller.

In response to a determination that the thermopile sensor does not correspond to a human being, no branch of 218, the alarm process is discontinued. The thermopile sensor terminates the working status, and the timer is reset to zero (220).

In response to a determination that the thermopile sensor does correspond to a human being, yes branch of 218, the controller triggers an alert response (222). For example, the alert response can be an alarm provided by a wireless RF circuit, e.g., wireless RF circuit 14 of FIG. 1, which transmits an alarm signal to a control center.

In some implementations, the determination of whether the current temperature and the background temperature are different is omitted. Instead, the process relies on the determination of whether the outline or shape of the area of the absorption region has a distinct current temperature relative to other areas of the absorption region and then the determination as to whether the outline or shape corresponds to a human being. In some other implementations, the threshold difference is based on the temperature measured within the area of the absorption region. In yet some other implementations, the threshold difference is based on a difference in current temperature measured within the area of the absorption region and current temperature measure outside the area.

The infrared detector includes both the pyroelectric sensor and the thermopile sensor in the same package. As a result, the infrared detector can determine whether a movable infrared signal source exists in the area being monitored as well as determine whether a static infrared signal source exists in the area being monitored. The infrared detector can determine, for example, whether a person falls down in the area being monitored. In addition, unlike a camera device, the thermopile sensor does not capture images, e.g., photographic images, which protects the privacy of those in the area being monitored. As such, the infrared detector can be installed in washing rooms, bedrooms, etc., and can be used to monitor those needing special care, e.g., those under nursing care.

Furthermore, the pyroelectric sensor and the thermopile sensor have low electrical energy consumption, and can therefore be constructed such that they only need a rechargeable battery instead of being plugged in or directly wired to a building electrical supply. Thus, the installation of the infrared detector is versatile.

In some alternative implementations, after the pyroelectric sensor is triggered, the set time of the timer may be adjusted depending upon an actual usage circumstances, or set manually. Alternatively, when the controller determines whether a static infrared signal source exists in the area being monitored, a threshold value for a difference between the background temperature and the current temperature may be set manually, e.g., based on particular criteria and environmental conditions.

The infrared detector described above can further be used for other applications including in advertisement boards or advertisement boxes. For example, the thermopile sensor first inspects a background temperature in an area under detection in front of an advertisement board or advertisement box. Then, the pyroelectric sensor determines whether anyone passes by, that is, the sensor detects whether the temperature in the area being monitored changes or not. If the temperature changes, the thermopile sensor detects the temperature in the area being monitored once again after a preset time period elapsed, and determines whether the current temperature is consistent with the background temperature. If not, it determines that someone stays in front of the advertisement board or advertisement box. In this case, the controller, used for controlling the advertisement board or advertisement box, controls the advertisement board or advertisement box to operate, e.g., powering on a screen to display images, characters, cartoons, or turning over a displaying board, etc.

Thus, when a person quickly walks by the front area of the advertisement board or advertisement box, the advertisement board or advertisement box does not display the advertising content or only shows a static advertising content. Only when someone stays in front of the advertisement board or advertisement box, the advertisement board or advertisement box operates, which reduces electrical energy consumed by the advertisement board or advertisement box.

It should be noted that, the infrared sensor described in this specification is not limited to be above implementations, and changing of the type of an alarm, the type of a timer, and the type of a rechargeable battery all fall within the protection scope as claimed. While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. An infrared detector, comprising:
   a pyroelectric sensor;
   a controller for receiving a trigger signal outputted by the pyroelectric sensor;
   a thermopile sensor, wherein the controller starts the thermopile sensor after receiving the trigger signal output by the pyroelectric sensor;
   a timer, wherein the controller starts the timer after receiving the trigger signal output by the pyroelectric sensor, and starts the thermopile sensor after a counted time is ended; and
   an alarm, wherein the controller controls the alarm to generate an alarm signal in response to a determination that a difference between a current temperature and a background temperature detected by the thermopile sensor is larger than a threshold value and a determination that the areas of the thermopile sensor activated correspond to a human being.

2. The infrared detector of claim 1, comprising a processing engine configured to analyze data from the thermopile sensor to determine whether a human being is detected.

3. The infrared detector of claim 1, comprising a processing engine configured to use a wireless circuit to communicate data from the thermopile sensor to a remote analysis location and to receive a result of the analysis.

4. The infrared detector of claim 1, wherein the alarm is a wireless alarm circuit.

5. The infrared detector of claim 4, wherein the wireless alarm circuit is a wireless radio frequency (RF) circuit, a Wi-Fi signal transmitting circuit, or a Bluetooth signal transmitting circuit.

6. The infrared detector of claim 1, further comprising:
   a battery module, for supplying power to the pyroelectric sensor and the thermopile sensor.

7. The infrared detector of claim 1, wherein the pyroelectric sensor detects entry of an individual to a region being monitored by the infrared sensor and wherein the thermopile sensor determines whether the individual remains in the region being monitored.

8. The method of claim 7, wherein in response to the timer time elapsing, using the thermopile sensor to determine the current temperature of the area being monitored.

9. The method of claim 7, wherein generating the alarm comprises using a wireless alarm circuit.

10. The method of claim 9, wherein the wireless alarm circuit is a wireless radio frequency (RF) circuit, a Wi-Fi signal transmitting circuit, or a Bluetooth signal transmitting circuit.

11. The infrared detector of claim 10, further comprising:
    a battery module, for supplying power to the pyroelectric sensor and the thermopile sensor.

12. A method comprising:
    using a thermopile sensor of an infrared detector to determine a background temperature of an area being monitored;
    using a pyroelectric sensor of the infrared detector to determine whether a temperature in the area being monitored has changed; and
    in response to a determination that the temperature has changed:
      using a thermopile sensor to determine a current temperature in the area being monitored including initiating a timer to count down a specified amount of time;
      comparing the determined current temperature to the background temperature; and
      based on the comparing, determining whether a difference between the determined current temperature and the background temperature satisfies a threshold value;
    in response to determining that the difference satisfies the threshold value, determining whether the thermopile sensor data corresponds to a human being; and
    in response to determining that the thermopile sensor data corresponds to a human being, generating an alarm.

13. The method of claim 12, wherein determining whether the thermopile sensor data corresponds to a human being comprises:
    determining the areas of an absorption region of the thermopile sensor triggered by infrared signals;
    determining an outline or shape of the areas; and
    determining whether the outline or shape of the areas corresponds to a human being.

14. The method of claim 12, wherein determining whether the thermopile sensor data corresponds to a human being comprises:
    compressing the thermopile sensor data;
    transmitting the compressed thermopile sensor data to a remote location; and
    receiving a determination of whether the thermopile sensor data corresponds to a human being from the remote location.

15. The method of claim 12, wherein in response to determining that the thermopile sensor data does not correspond to a human being, discontinuing the alarm process.

16. An infrared detector, comprising:
    a pyroelectric sensor;
    a controller for receiving a trigger signal outputted by the pyroelectric sensor;
    a thermopile sensor, wherein the controller starts the thermopile sensor after receiving the trigger signal output by the pyroelectric sensor; and
    an alarm, wherein the alarm is triggered by the controller in response to determining that detected signals from the thermopile sensor correspond to a human being;
    wherein the pyroelectric sensor detects entry of an individual to a region being monitored by the infrared sensor and wherein the thermopile sensor determines whether the individual remains in the region being monitored.

17. The infrared detector of claim 16, further comprising:
    a timer, wherein the controller starts the timer after receiving the trigger signal output by the pyroelectric sensor, and starts the thermopile sensor after a counted time is ended.

18. The infrared detector of claim 16, wherein the alarm is a wireless alarm circuit.

19. The infrared detector of claim 18, wherein the wireless alarm circuit is a wireless radio frequency (RF) circuit, a Wi-Fi signal transmitting circuit, or a Bluetooth signal transmitting circuit.

20. A method comprising:
    using a thermopile sensor of an infrared detector to determine a background temperature of an area being monitored;
    using a pyroelectric sensor of the infrared detector to determine whether a temperature in the area being monitored has changed wherein the pyroelectric sensor detects entry of an individual to a region being monitored by the infrared detector; and
    in response to a determination by the pyroelectric sensor that the temperature has changed using the thermopile sensor to determine whether the individual remains in the region being monitored:

using a thermopile sensor to determine a current temperature in the area being monitored;

determining an outline or shape of an area of an absorption region of the thermopile sensor in which the current temperature is different from the background temperature;

determining whether the outline or shape corresponds to a human being; and in response to determining that the outline or shape corresponds to a human being, generating an alarm.

21. The method of claim 20, comprising determining whether the difference between the current temperature in the area and the background temperature satisfies a threshold value.

* * * * *